()# United States Patent
Schouteeten et al.

(10) Patent No.: US 7,544,817 B2
(45) Date of Patent: Jun. 9, 2009

(54) PROCESS FOR THE PREPARATION OF N-ALKYL-2(HYDROXY-4BENZOYL)-3 BENZOFURANS AND INTERMEDIATES THEREOF

(75) Inventors: Alain Schouteeten, Ezanville (FR); François Bleger, Trosly-Breuil (FR); Françoise Mordacq, Trosly-Breuil (FR); Jérôme Piron, Janville (FR)

(73) Assignee: Clariant (France), Puteaux (FR)

( * ) Notice: Subject to any disclaimer, the term of this patent is extended or adjusted under 35 U.S.C. 154(b) by 0 days.

(21) Appl. No.: 10/584,440

(22) PCT Filed: Dec. 15, 2004

(86) PCT No.: PCT/IB2004/004158

§ 371 (c)(1),
(2), (4) Date: Nov. 29, 2006

(87) PCT Pub. No.: WO2005/066149

PCT Pub. Date: Jul. 21, 2005

(65) Prior Publication Data

US 2007/0155831 A1   Jul. 5, 2007

(30) Foreign Application Priority Data

Dec. 24, 2003   (FR) .................. 03 15398

(51) Int. Cl.
*C07D 307/00* (2006.01)
(52) U.S. Cl. .................. 549/468
(58) Field of Classification Search .......... 549/469, 549/468
See application file for complete search history.

(56) References Cited

U.S. PATENT DOCUMENTS

| 3,983,245 A | 9/1976 | Ladd |
| 5,223,510 A | 6/1993 | Gubin |
| 5,854,282 A | 12/1998 | Mellin |
| 6,515,147 B2 * | 2/2003 | Schouteeten et al. ........ 549/304 |

FOREIGN PATENT DOCUMENTS

DE   2347196 A1 *  9/1973
WO   WO 99/58519   11/1999

OTHER PUBLICATIONS

Bisagni et al. STN Accession No. 1961:76079 Document No. 55:76079 Abstract of Bulletin de la Societe Chimique de France (1960), 1968-76.*
Gubin et al.STN Accession No. 1974:437442 Document No. 81:37442, Abstract of European Journal of Medicinal Chemistry (1974), 9(1), 19-25.*
Benassi et al. STN Accession No. 108:21130, Abstract of Journal of the Chemical Society, Perkin Transactions 2: Physical Organic Chemistry (1972-1999) (1987), (3), 351-7.*
Chatterjea (Journal of Indian Chemical Society, 1957, vol. 34 (4), 299-305).*
Powers, Larry J., "Chemistry and antibacterial activity of nitrobenzofurans", Journ. of Medicinal Chemistry, (1976), 19(1), pp. 57-62.
International Search Report for PCT/IB2004/004158, Mailed Jan. 31, 2005.
PCT IPER for PCT/IB2004/004158, Mailed Jan. 31, 2005.

* cited by examiner

*Primary Examiner*—D. Margaret Seaman
*Assistant Examiner*—Nizal S Chandrakumar
(74) *Attorney, Agent, or Firm*—Richard P. Silverman

(57) ABSTRACT

Process for the preparation of a 2-(n-alkyl)-3-(4-hydroxybenzoyl)benzofuran of formula (I)

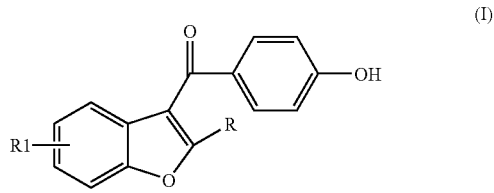

in which R represents a linear or branched alkyl radical including from 1 to 5 carbon atoms and R1 represents a linear or branched alkyl radical including from 1 to 3 carbon atoms, a linear or branched alkoxy radical including from 1 to 3 carbon atoms, a halogen atom or a nitro radical, and intermediates.

5 Claims, No Drawings

PROCESS FOR THE PREPARATION OF N-ALKYL-2(HYDROXY-4BENZOYL)-3 BENZOFURANS AND INTERMEDIATES THEREOF

The present invention relates to a novel process for the preparation of 2-(n-alkyl)-3-(4-hydroxybenzoyl)benzofurans and intermediates for its implementation.

There is always a search for alternative routes for the preparation of 2-(n-alkyl)-3-(4-hydroxybenzoyl)benzofurans and in particular of 2-(n-butyl)-3-(4-hydroxybenzoyl)-5-nitrobenzofuran, an intermediate for the antiarrhythmic dronedarone.

In FR-A-2 665 444, 2-(n-butyl)-3-(4-hydroxybenzoyl)-5-nitrobenzofuran is prepared by the reaction of 2-(n-butyl)-5-nitrobenzofuran (NBBF) with anisoyl chloride in the presence of tin tetrachloride in dichloroethane and then reaction with aluminium chloride in dichloroethane.

The major problem of this synthesis is the use of p-anisic acid or its acid chloride, which are expensive reactants.

Moreover, NBBF can be prepared from 2-coumaranone, according to the technique disclosed in FR-A-2 803 846, or from 2-hydroxybenzaldehyde.

According to FR-A-2 803 846, NBBF can be obtained by reacting 2-coumaranone with pentanoic anhydride and a pentanoic acid salt to produce a mixture of tautomers (3-(1-hydroxypentylidene)-5-nitro-3H-benzofuran-2-one and 3-pentanoyl-5-nitro-3H-benzofuran-2-one) which is subjected to the action of 40% sulphuric acid in acetic acid to produce the expected NBBF.

It would therefore be desirable to have available a process for the preparation of 2-(n-alkyl)-3-(4-hydroxybenzoyl)benzofurans and particularly of 2-(n-butyl)-3-(4-hydroxybenzoyl)-5-nitrobenzofuran which has a good yield, which is simple to carry out and which results in a product with a good purity.

In point of fact, after lengthy research, the Applicant Company has discovered with astonishment that the reaction of 3-(1-hydroxyalkylidene)-3H-benzofuran-2-one compounds or their 3-alkanoyl-3H-benzofuran-2-one ketonic tautomeric forms in the presence of a concentrated acid catalyst promotes the formation of 2-(n-alkyl)-3-carboxybenzofurans.

Another surprising component of this synthetic route is the selective reaction in the para position of a phenol ether, unsubstituted in the 2 and 6 positions, in a Friedel-Crafts reaction, making it possible to obtain essentially a 4-alkoxy derivative and very little 2-alkoxy derivative.

This distinctive feature makes it possible to carry out the dealkylation stage on the mixture of the 4-alkoxy derivative and of the 2-alkoxy derivative without having to perform a preliminary separation and to obtain the desired product with a good yield and a good purity.

For this reason, a subject-matter of the present application is a process for the preparation of a 2-(n-alkyl)-3-(4-hydroxybenzoyl)benzofuran of formula (I)

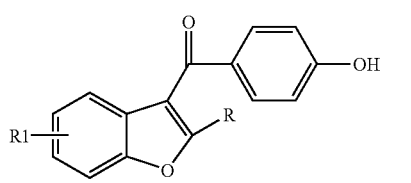
(I)

in which R represents a linear or branched alkyl radical including from 1 to 5 carbon atoms and R1 represents a linear or branched alkyl radical including from 1 to 3 carbon atoms, a linear or branched alkoxy radical including from 1 to 3 carbon atoms, a halogen atom or a nitro radical, in which a) a 2-alkyl-3-carboxybenzofuran of formula (II)

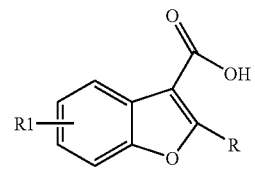
(II)

in which R and R1 have the meanings already indicated, is reacted with a halogenating agent to produce the compound of formula (III)

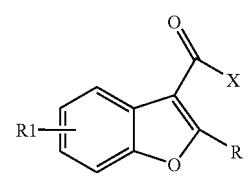
(III)

in which X represents a halogen atom and R and R1 have the meanings already indicated, b) then the compound of formula (III) is reacted with an alkyl phenyl ether of formula

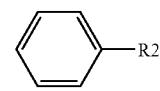

in which R2 represents a linear or branched alkoxy radical including from 1 to 5 carbon atoms, in the presence of a Lewis acid, to produce a mixture of 2-alkyl-3-(4-alkoxybenzoyl)benzofuran of formula (IV) and of 2-alkyl-3-(2-alkoxybenzoyl)benzofuran of formula (IVa)

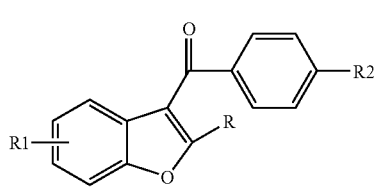
(IV)

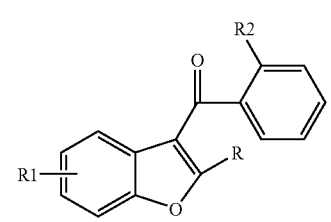
(IVa)

in which R, R1 and R2 have the meanings already indicated, c) and the mixture is subjected to a dealkylation reaction to produce the product of formula (I), which is isolated, if desired.

In the formula (I) and in what follows, the term "linear or branched alkyl radical including from 1 to 3 carbon atoms" represents, for example, a propyl, ethyl or methyl radical. The term "linear or branched alkyl radical including from 1 to 5 carbon atoms" represents, for example, an n-pentyl, n-propyl or ethyl radical, preferably an n-butyl radical. The term "linear or branched alkoxy radical including from 1 to 5 carbon atoms" represents, for example, a propoxy or ethoxy radical, preferably a methoxy radical. The term "halogen atom" or "the X substituent" represents, for example, an iodine or bromine atom, preferably a chlorine atom.

The benzofuran ring system can comprise 4 R1 radicals, preferably 2 R1 radicals and particularly just 1 R1 radical.

The R1 radical is preferably situated in the 5 or 7 position and particularly in the 5 position.

Use may be made, as halogenating agent, for example, of phosphorus trichloride $PCl_3$, phosphorus pentachloride $PCl_5$, phosphorus oxychloride $POCl_3$, oxalyl chloride $(COCl)_2$, phosgene $COCl_2$ and, particularly, thionyl chloride $SOCl_2$.

Under preferred conditions for implementing the invention, the amount of halogenating agent employed is such that the halogenating agent/compound of formula (II) molar ratio has a value from 1 to 5, preferably from 1.1 to 2.

Under other preferred conditions for implementing the invention, the halogenation reaction takes place at a temperature lying between ambient temperature and the reflux temperature of the reaction medium.

Under yet other preferred conditions for implementing the invention, the reaction of the 2-alkyl-3-carboxybenzofuran of formula (II) with the halogenating agent is carried out in the presence of an organic solvent which is advantageously a halogenated aliphatic and/or aromatic hydrocarbon, particularly chlorobenzene, or an alkyl phenyl ether, particularly anisole.

Under preferred conditions for implementing the invention, the amount of alkyl phenyl ether employed is such that the alkyl phenyl ether/compound of formula (III) molar ratio ranges from 1 to 10, preferably from 1 to 2, and in particular is equal to approximately 1.2.

Under other preferred conditions for implementing the invention, the temperature of the reaction between the compound of formula (III) and the alkyl phenyl ether is between −5° C. and ambient temperature, preferably between 0° C. and 5° C.

This reaction is advantageously carried out in the presence of an organic solvent which is preferably a halogenated aliphatic and/or aromatic hydrocarbon, particularly chlorobenzene, or an alkyl phenyl ether, particularly anisole.

The Lewis acid used in the reaction between the compound of formula (III) and the alkyl phenyl ether can, for example, be an aluminium halide, a boron halide, a titanium halide, a tin halide, a bismuth halide or an iron halide, and preferably aluminium chloride.

Under preferred conditions for implementing the invention, the amount of Lewis acid employed is such that the Lewis acid/compound of formula (III) molar ratio ranges from 1 to 10, preferably from 1 to 1.5, and in particular is equal to approximately 1.2.

Use may be made, in carrying out the dealkylation, for example, of the techniques described in Greene, T. W., Protective Groups in Organic Synthesis, Chapter 3, John Wiley and Sons, New York, 3rd edition, 1999, pages 250-254.

Preferably, use is made, as dealkylating agent, of pyridine hydrochloride, hydriodic acid or hydrobromic acid and, in particular, heating is carried out in the presence of a Lewis acid.

The Lewis acid used in the dealkylation reaction can be, for example, an aluminium halide, a boron halide, a titanium halide, a tin halide, a bismuth halide or an iron halide and preferably aluminium chloride.

Under preferred conditions for implementing the invention, the amount of Lewis acid employed in the dealkylation stage is such that the Lewis acid/compound of formula (IV) and (IVa) molar ratio ranges from 1 to 10, preferably from 2 to 5, and in particular is equal to approximately 3.

The heating temperature in the dealkylation stage can range from 40° C. to 100° C., preferably from 50° C. to 65° C.

The dealkylation is carried out in particular in the presence of an organic solvent which is preferably a halogenated aliphatic and/or aromatic hydrocarbon, more particularly chlorobenzene.

The compounds of formula (II) can be prepared by treatment of 3-(1-hydroxyalkylidene)-3H-benzofuran-2-one compounds or their 3-alkanoyl-3H-benzofuran-2-one ketonic tautomeric forms using an acid catalyst in concentrated aqueous solution at 80 to 95%, for example using 90% concentrated sulphuric acid, preferably in a carboxylic acid and in particular in acetic acid.

The intermediate compounds of formulae (II) and (III) have very advantageous properties. They readily result, by a Friedel-Crafts reaction, essentially in a 4-alkoxy derivative and very little 2-alkoxy derivative, generally in a ratio of 95/5 to 97/3.

This unexpected property makes it possible to carry out the dealkylation stage on the mixture of the 4-alkoxy derivative and of the 2-alkoxy derivative without having to perform a preliminary separation and thus to obtain the desired product with a good yield and a good purity.

For this reason, another subject-matter of the present application is a compound of formula (V)

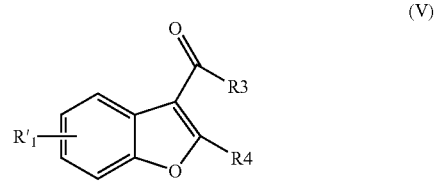

(V)

in which R3 represents a hydroxyl radical or, preferably, has the meaning of X, R4 represents a linear or branched alkyl radical including from 2 to 5 carbon atoms and R'$_1$ represents a nitro radical.

The term "linear or branched alkyl radical including from 2 to 5 carbon atoms" represents, for example, an ethyl, n-propyl or pentyl radical and preferably an n-butyl radical.

The benzofuran ring system can comprise 2 R'$_1$ radicals and preferably just 1 R'$_1$ radical.

The R'$_1$ radical is preferably situated in the 5 or 7 position and particularly in the 5 position.

Finally, a subject-matter of the present application is a process for the preparation of the 2-(n-alkyl)-3-carboxybenzofurans of formula (II), characterized in that a 3-(1-hydroxyalkylidene)-3H-benzofuran-2-one of formula (VI):

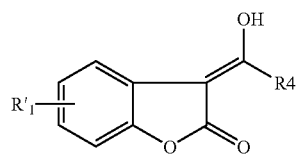

(VI)

or its 3-alkanoyl-3H-benzofuran-2-one ketonic tautomeric form of formula (VII):

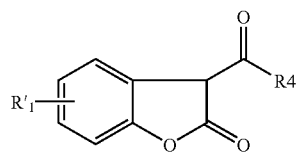

(VII)

in which R4 has the meaning already indicated and R'$_1$ has the meaning already indicated, is treated by heating, preferably in a carboxylic acid, in particular in acetic acid, and by an acid catalyst in a concentrated aqueous solution at at least 80% by weight, preferably between 80% and 95% by weight, for example a Brönsted acid, such as hydrochloric acid and particularly sulphuric acid, at between 80% and 95% by weight, in particular 90% concentrated, and then in that the expected product of formula (II) is isolated.

The reaction can be carried out at atmospheric pressure or under pressure.

The preferred conditions for implementing the process which are described above also apply to the other subject-matters of the invention targeted above, in particular to the compounds of formula (V).

The following examples illustrate the present patent application.

EXAMPLE 1

Preparation of 2-(n-butyl)-3-(4-hydroxybenzoyl)-5-nitrobenzofuran

Stage A 133 g of 2-(n-butyl)-3-carboxy-5-nitrobenzofuran are charged, with stirring and under an anhydrous atmosphere, to a reactor comprising 400 g of chlorobenzene.

After having brought the mixture to a temperature in the region of 80° C., 108 g of thionyl chloride are added over approximately 20 minutes and then the reaction medium is maintained at a temperature in the region of 80° C. with stirring for 9 hours.

The excess thionyl chloride and a portion of the chlorobenzene are distilled off under vacuum without the temperature in the distillation vessel exceeding 80° C.

After distilling off 150 g of mixture, the acid chloride solution (approximately 360 g) is cooled and is used as is in the following stage.

Stage B 350 g of chlorobenzene and 80 g of aluminium chloride are introduced into another reactor, which is then cooled to a temperature in the region of 0° C.

61 g of anisole are added at this temperature over 15 minutes and then the acid chloride solution from Stage A is added over approximately 1 hour while maintaining the temperature of the reaction medium below 5° C.

The temperature is allowed to rise to approximately 20° C. over approximately 1 hour.

After stirring at ambient temperature for 3 hours, the formation of 171 g of 2-(n-butyl)-3-(4-methoxybenzoyl)-5-nitrobenzofuran and 4 g of 2-(n-butyl)-3-(2-methoxybenzoyl)-5-nitrobenzofuran is quantitatively determined by HPLC (high performance liquid chromatography) with external calibration.

Stage C 680 g of chlorobenzene and 120 g of aluminium chloride are added and the reaction medium is heated at 60° C. for 7 hours.

The medium is subsequently hydrolysed with 400 g of water. Separation by settling is allowed to take place at a temperature in the region of 60° C. and the organic phase is extracted three times with 600 g of water at 60° C.

The resulting organic phase is dried by azeotropic distillation under reduced pressure at 60° C.

The medium is allowed to cool to ambient temperature and is then maintained at 3° C. for 2 hours.

The solid product is filtered off and then washed with 360 g of chlorobenzene.

After drying under reduced pressure to constant weight, 138.5 g of 2-(n-butyl)-3-(4-hydroxybenzoyl)-5-nitrobenzofuran are obtained in the form of a greyish beige solid assaying at 99.5% by acidimetry.

$^1$H NMR (CDCl$_3$): δ 0.8 (t, J=7.6 Hz, 3H); δ 1.3 (s, J=7.6 Hz, 2H); δ 6 1.7 (q, J=7.6 Hz, 2H); δ 2.8 (t, J=7.6 Hz, 2H); δ 5.5 (s, 1 H); δ 7.7 and 6.9 (AB system, J$_{AB}$=7Hz, 4H); δ 7.5 (d, J=9Hz, 1H) ;δ 8.15 (dd, J=2.4Hz, J=9Hz, 1H); δ 8.26 (d, J=2.4Hz, 1H)

Preparation of 2-(n-butyl)-3-carboxy-5-nitrobenzofuran

The starting 2-(n-butyl)-3-carboxy-5-nitrobenzofuran can be prepared in the following way:

263 g of 3-(1-hydroxypentylidene)-5-nitro-3H-benzofuran-2-one, 480 g of acetic acid and 190 g of 90% concentrated sulphuric acid are charged to a three-necked round-bottomed flask.

The mixture is brought to reflux for 2 hours with stirring, the internal temperature being in the region of 127-128° C.

The reaction medium is cooled to the region of 10° C. and then the precipitate is filtered off.

The solid obtained is washed with 10 g of acetic acid and then with 300 g of water.

After drying, 202.5 g of beige product are obtained, which product assays at 99% by acidimetry.

Melting point: 207° C. (DSC, Mettler 2673, 3° C./min)

$^1$H NMR (d$_6$-DMSO): δ 0.90 (t, J=7.6 Hz, 3H); δ 1.30 (m, 2H); δ 1.70 (m, 2H); δ 3.19 (t, J=7.6 Hz, 2H); δ 7.83 (d, J=9 Hz, 1H); δ 8.20 (dd, J=2.5 Hz, J=9Hz, 1H); δ 8.66 (d, J=2.5Hz, 1H).

EXAMPLE 2

Preparation of 2-(n-butyl)-3-(4-hydroxybenzoyl)-5-nitrobenzofuran

Stage A 56 g of 2-(n-butyl)-3-carboxy-5-nitrobenzofuran are charged, with stirring and under an anhydrous atmosphere, to a reactor comprising 116 g of anisole.

After having brought the mixture to a temperature in the region of 80° C., 28 g of thionyl chloride are added over approximately 20 minutes and then the reaction medium is maintained at a temperature in the region of 80° C. for 3 hours with stirring.

The excess thionyl chloride and a portion of the anisole are distilled off under reduced pressure without the temperature in the distillation vessel exceeding 80° C.

After distilling off 6 g of mixture, the acid chloride solution (approximately 170 g) is cooled.

Stage B 80 g of anisole are introduced into another reactor, cooling is carried out to approximately 0° C., 34 g of aluminium chloride are then added and the preceding acid chloride solution, cooled to 0° C., is added over approximately 1 hour with stirring without the temperature of the reaction medium exceeding 5° C., and then the reaction medium is allowed to return to ambient temperature.

After stirring at this temperature for 1 hour, the formation of 71 g of 2-(n-butyl)-3-(4-methoxybenzoyl)-5-nitrobenzofuran and 2.4 g of 2-(n-butyl)-3-(2-methoxybenzoyl)-5-nitrobenzofuran is quantitatively determined by HPLC (high performance liquid chromatography) with external calibration.

Stage C

The suspension is distilled under 40 mm of mercury, so as to maintain the temperature of the reaction medium below 65° C. After distilling off 130 g of anisole, the residue is taken up in 550 g of chlorobenzene, 69 g of aluminium chloride are then added and the reaction medium is brought to a temperature in the region of 60° C. with stirring.

After 7 hours at this temperature, the medium is hydrolysed with 170 g of water while maintaining the temperature at approximately 60° C. and then, after separation by settling, the organic phase is washed three times with 250 g of water at a temperature in the region of 60° C.

HPLC analysis of the resulting organic phase shows the formation of 66.4 g of 2-(n-butyl)-3-(4-hydroxybenzoyl)-5-nitrobenzofuran and of 2.3 g of 2-(n-butyl)-3-(2-hydroxybenzoyl)-5-nitrobenzofuran.

By proceeding in the same way as in Example 2, 53.8 g of 2-(n-butyl)-3-(4-hydroxybenzoyl)-5-nitrobenzofuran are recovered, which product assays at 99.4% by acidimetry.

EXAMPLE 3

Preparation of
2-(n-butyl)-3-chlorocarbonyl-5-nitrobenzofuran 133 g of 2-(n-butyl)-3-carboxy-5-nitrobenzofuran are charged, with stirring and under an anhydrous atmosphere, to a reactor comprising 400 g of chlorobenzene.

After having brought the mixture to a temperature in the region of 80° C., 108 g of thionyl chloride are added over approximately 20 minutes and then the reaction medium is maintained at a temperature in the region of 80° C. for 9 hours with stirring.

The excess thionyl chloride and a portion of the chlorobenzene are distilled off under vacuum without the temperature in the distillation vessel exceeding 80° C.

After distilling off 150 g of mixture, the acid chloride solution (approximately 360 g) is cooled.

850 g of n-heptane are added with stirring and the reaction mixture is cooled at 0° C. for 1 h. The precipitate obtained is filtered off, washed with 1 liter of n-heptane and then dried under vacuum with the exclusion of moisture.

85 g of the expected acid chloride are obtained.

Melting point: 66.2° C. (DSC, Mettler 2673, 5° C./min).

$^1$H NMR (CDCl$_3$): δ 0.95 (t, J=7.6 Hz, 3H); δ 1.45 (m, J=7.6 Hz, 2H); δ 1.8 (m, J=7.6 Hz, 2H); δ 3.23 (t, J=7.6 Hz, 2H); δ 7.6 (d, J=9.1 Hz, 1H); δ 8.3 (dd, J1=9.1 Hz, J2=2.3Hz, 1H); δ 9.0 (d, J=2.3Hz, 1H).

The invention claimed is:

1. A compound of formula (V)

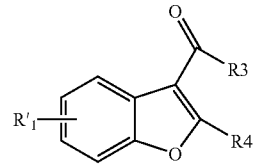

in which R3 represents a hydroxyl radical or represents a halogen atom, R4 represents a linear or branched alkyl radical including from 2 to 5 carbon atoms and R'$_1$ represents a nitro radical.

2. The compound according to claim 1, characterized in that R'$_1$ represents a nitro radical in the 5 position and R4 represents an n-butyl radical.

3. A process for the preparation of a 2-(n-alkyl)-3-carboxybenzofuran of formula (II), characterized in that a 3-(1-hydroxyalkylidene)-3H-benzofuran-2-one of formula (VI):

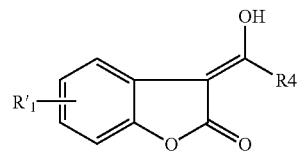

or its 3-alkanoyl-3H-benzofuran-2-one ketonic tautomeric form of formula (VII):

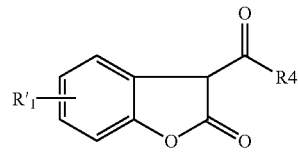

in which R4 represents a linear or branched alkyl radical including from 2 to 5 carbon atoms and R'$_1$ represents a nitro radical, is treated by heating and by an acid catalyst in concentrated aqueous solution of at least 80% by weight and then the expected product of formula (II)

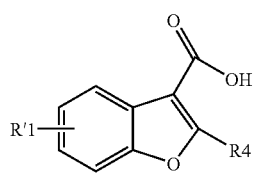 (II)
is isolated.
4. Process according to claim 3, characterized in that the treatment by heating of the compound of formula (VI) or of formula (VII) is carried out in a carboxylic acid.
5. The process of claim 3, wherein the acid catalyst in concentrated aqueous solution is concentrated sulphuric acid at between 80% and 95% by weight.
* * * * *